(12) United States Patent
Zhao et al.

(10) Patent No.: US 10,151,697 B2
(45) Date of Patent: Dec. 11, 2018

(54) TWO-COLOR FLUORESCENCE LOCALIZATION SUPER-RESOLUTION BIOLOGICAL MICROSCOPY METHOD AND SYSTEM

(71) Applicant: Shenzhen NanoBioImaging Limited, Shenzhen, Guangdong Province (CN)

(72) Inventors: Teng Zhao, Hong Kong (CN); Michael M. T. Loy, Hong Kong (CN); Shengwang Du, Hong Kong (CN)

(73) Assignee: Shenzhen NanoBioImaging Limited, Shenzhen (CN)

( * ) Notice: Subject to any disclaimer, the term of this patent is extended or adjusted under 35 U.S.C. 154(b) by 0 days.

(21) Appl. No.: 15/303,461

(22) PCT Filed: Sep. 7, 2015

(86) PCT No.: PCT/CN2015/089047
§ 371 (c)(1),
(2) Date: Oct. 11, 2016

(87) PCT Pub. No.: WO2016/095572
PCT Pub. Date: Jun. 23, 2016

(65) Prior Publication Data
US 2017/0284941 A1  Oct. 5, 2017

(30) Foreign Application Priority Data
Dec. 17, 2014  (CN) .......................... 2014 1 0787361

(51) Int. Cl.
*G01N 21/64* (2006.01)
(52) U.S. Cl.
CPC ..... *G01N 21/6428* (2013.01); *G01N 21/6458* (2013.01); *G01N 2021/6441* (2013.01); *G01N 2201/06113* (2013.01)

(58) Field of Classification Search
CPC ........... G01N 21/6428; G01N 21/6458; G01N 2201/06113; G01N 2021/6441
(Continued)

(56) References Cited

U.S. PATENT DOCUMENTS 7,153,692 B2 *  12/2006  Campbell ............ G01N 33/493
436/90
8,536,543 B2   9/2013  Iketaki
(Continued)

FOREIGN PATENT DOCUMENTS

CN    101587238 A    6/2009
CN    104122662 A    10/2014
(Continued)

OTHER PUBLICATIONS

ThermoFisher Scientific, 2010, Molecular Probes Handbook—Chapter 2 Thiol-Reactive Probes, p. 104-106.*
(Continued)

*Primary Examiner* — David Porta
*Assistant Examiner* — Gisselle Gutierrez
(74) *Attorney, Agent, or Firm* — Greer, Burns & Crain, Ltd.

(57) ABSTRACT

A two-color fluorescence localized super-resolution biological microscopy method and system are disclosed. The method includes: performing two-color fluorescence labeling on a biological sample by using Alexa647 and Alexa750 fluorescent molecules or Cy5 and Cy7 fluorescent molecules, and soaking the biological sample in an imaging buffer solution; illuminating the biological sample by laser to generate a flashing fluorescent signal of a first channel and a flashing fluorescent signal of a second channel respectively; constructing a super-resolution image of a first biological structure and a super-resolution image of a second biological structure respectively; and aligning the super-
(Continued)

resolution image of the first biological structure and the super-resolution image of the second biological structure so as to construct a super-resolution image of a third biological structure. Thereby, the present method and system do not generate channel crosstalk and can significantly reduce background noise, so that the imaging quality is improved.

17 Claims, 5 Drawing Sheets

(58) Field of Classification Search
USPC .......................................... 250/459.1, 458.1
See application file for complete search history.

(56) References Cited

U.S. PATENT DOCUMENTS

| | | | | |
|---|---|---|---|---|
| 2006/0147948 | A1* | 7/2006 | Keillor | G01N 33/582 435/6.16 |
| 2010/0303386 | A1 | 12/2010 | Enderlein | |
| 2010/0310246 | A1* | 12/2010 | Campbell | G03B 7/085 396/89 |
| 2012/0001058 | A1* | 1/2012 | Luke | G01J 1/4228 250/208.2 |
| 2012/0062722 | A1* | 3/2012 | Sase | G01N 21/6458 348/79 |
| 2012/0214194 | A1* | 8/2012 | Franck | C07D 307/58 435/40.5 |
| 2014/0198198 | A1 | 7/2014 | Geissbuehler et al. | |
| 2015/0140123 | A1* | 5/2015 | Mueller | G01N 33/5014 424/649 |
| 2015/0276602 | A1* | 10/2015 | Ishihara | A61B 1/00009 250/458.1 |
| 2016/0299069 | A1* | 10/2016 | Tao | G01N 21/553 |
| 2017/0360940 | A1* | 12/2017 | Finn | C08J 3/24 |

FOREIGN PATENT DOCUMENTS

| | | | | |
|---|---|---|---|---|
| CN | 104122662 | * | 12/2014 | ............. G02B 21/36 |
| KR | 1020080054647 | A | 6/2008 | |

OTHER PUBLICATIONS

Tang et al., Oct. 1, 2014, Sub-nanometer drift correction for super-resolution imaging, Optics Letters, vol. 36, No. 19, pp. 5685-5686.*

International Search Report from International Patent Application No. PCT/CN2015/089047, dated Dec. 9, 2015.

* cited by examiner

TWO-COLOR FLUORESCENCE LOCALIZATION SUPER-RESOLUTION BIOLOGICAL MICROSCOPY METHOD AND SYSTEM

BACKGROUND

The invention relates to the field of biological microscopy, in particular to two-color-fluorescence localized super-resolution biological microscopy method and system.

Since Ernst Abbe proposed the theory of optical imaging resolution limit in the 1770s, people have been looking for ways to break the resolution limit. Through single molecule fluorescence localization, Zhuang Xiaowei and Eric Betzig successively put forward Stochastic Optical Reconstruction Microscopy (STORM) and Photoactivated Localization Microscopy (PALM) respectively in 2006 realizing super-resolution of ten times the optical resolution limit. Eric Betzig won the Nobel Prize in Chemistry 2014 by the PALM. The fluorescence localization microscopies have been partially commercialized, and applied to researches of fundamental life science, especially molecular biology and biochemistry. Researchers can investigate detailed structures of biological samples at lateral resolution of 10 to 20 nm and vertical resolution of 50 nm by these techniques. Compared with other existing super-resolution techniques such as electron microscopy, the fluorescence localization microscopies greatly simplify the preparation process of samples, and can realize the live-cell imaging. What's more, the fluorescence localization microscopies can easily realize multi-channel co-localization imaging, and thus obtain the interaction between proteins, providing the most immediate evidences for a large number of molecular bioresearch topics. However, the performance of existing techniques in multi-color super-resolution imaging still has shortcomings. As a representation of the commercial fluorescence localization microscopies, two-channel imaging of Nikon N-STORM uses fluorescent switches combining two fluorescent molecules (e.g., Alexa647-Alexa488 molecular pair and Alexa467-Alexa405 molecular pair) with different excitation wavelengths as markers. The method can realize quick switch between different imaging channels, but the markers of such fluorescent switches are not currently commercialized, and preparation thereof in laboratory is relatively complicated. What's more, the two-color imaging method will produce severe channel crosstalk, and produce wrong co-localization information. Leica SR GSD uses ordinary fluorescent molecules (e.g., Alexa647 and Alexa532) with different excitation wavelengths as markers, and uses a filter system to realize two-channel imaging. The limitation of the method is that fluorescent molecules with short excitation wavelengths are easy to be photo-bleached, and the short excitation wavelengths will lead to autofluorescence background of cells, which affects the imaging quality.

In addition, sample drift is a common problem in super-resolution fluorescence localization microscopies, which means that samples will move tens to hundreds of nanometers during shooting due to environmental instability such as airflow, temperature change and noise. Although the drift is common in microscopy systems, the drift is not obvious as the resolution of an ordinary microscope is less than 300 nm. But for a super-resolution microscope with resolution up to dozens of nanometers, the drift will severely interfere with imaging. Most of existing solutions are to add fluorescent particles in samples, record displacement of the particles in imaging, and subsequently subtract the displacement from obtained super-resolution images. The defects are difficult preparation and the fluorescent particles will also occupy an imaging channel. Besides, fluorescence of the fluorescent particles will attenuate over imaging time due to photo-bleaching, therefore, the correction precision of drift gets worse over time.

To sum up, existing techniques have obvious inconvenience and defects in practice, so improvement is necessary.

SUMMARY

With respect to the above-mentioned defects, the purpose of the invention is to provide method and system of a two-color fluorescence localized super-resolution biological microscopy, which do not have channel crosstalk and can significantly reduce background noise, thus improving imaging quality.

In order to realize the purpose, the invention provides a two-color fluorescence localized super-resolution biological microscopy method, which comprises the following steps:

performing two-color fluorescence labeling on a biological sample by using Alexa647 and Alexa750 fluorescent molecules or Cy5 and Cy7 fluorescent molecules, and soaking the biological sample in an imaging buffer solution;

illuminating the biological sample by lasers to generate a blinking fluorescent signal of a first channel corresponding to the Alexa647 or Cy5 fluorescent molecules as well as a blinking fluorescent signal of a second channel corresponding to the Alexa750 or Cy7 fluorescent molecules respectively;

constructing a super-resolution image of a first biological structure and a super-resolution image of a second biological structure according to the blinking fluorescent signals of the first channel and the second channel respectively;

aligning the super-resolution image of the first biological structure and the super-resolution image of the second biological structure to construct a super-resolution image of a third biological structure.

According to the method of the invention, the step of illuminating the biological sample by laser further comprises the following step:

illuminating the biological sample by the specified activation laser to activate the fluorescent signal, and illuminating the biological sample by the specified excitation laser to deactivate the fluorescent signal so as to generate the blinking fluorescent signal.

According to the method of the invention, the activation laser has a violet or ultraviolet wavelength; the excitation laser has an excitation wavelength of the Alexa647 and Alexa750 fluorescent molecules, or the excitation laser has an excitation wavelength of the Cy5 and Cy7 fluorescent molecules; and the specified excitation laser power and activation laser power are used to disable most fluorescent molecules to emit fluorescent signals at the same time, leaving a small number of discrete fluorescent molecules to emit fluorescent signals.

According to the method of the invention, the imaging buffer solution comprises TCEP, cyclooctatetraene, deoxidant, methyl viologen and/or ascorbic acid; or the imaging buffer solution comprises sulfydryl compounds cyclooctatetraene, deoxidant, methyl viologen and/or ascorbic acid.

According to the method of the invention, the TCEP or sulfydryl compounds and the fluorescent molecules are combined to form an adduct under illumination of the excitation laser, the adduct does not fluoresce under illumination of the excitation laser, the adduct is redecomposed into the TCEP or Thio and the fluorescent molecules under illumination of the activation laser, and the fluorescent molecules fluoresce.

According to the method of the invention, the cyclooctatetraene comprises derivatives thereof, the deoxidant comprises a combination of glucose oxidase, glucose and catalase, or the deoxidant comprises a combination of pyranose oxidase, glucose and catalase.

According to the method of the invention, the method further comprises the following steps before the step of constructing super-resolution images of a first biological structure and a second biological structure according to the blinking fluorescent signals of the first channel and the second channel respectively:

locking the location of the biological sample by a real-time locking system before data acquisition According to the method of the invention, the step of locking the location of the biological sample by a real-time locking system further comprises the following steps:

providing wide-field illumination for the biological sample, and get wide-field imaging of the biological sample in a locking camera through a front imaging lens;

capturing a wide-field image of the biological sample or reference object from the locking camera as the locking template;

capturing a current wide-field image of the biological sample in real time from the locking camera, and comparing the current wide-field image with the locking template;

calculating offset between the current wide-field image and the locking template;

performing offset compensation on the current wide-field image according to the calculated offset.

According to the method of the invention, the step of constructing the super-resolution image of the first biological structure and the super-resolution image of the second biological structure according to the blinking fluorescent signal of the first channel and the blinking fluorescent signal of the second channel respectively further comprises the following steps:

acquiring the blinking fluorescent signal of the first channel and the blinking fluorescent signal of the second channel by a two-color fluorescence localized super-resolution microscope;

separating the blinking fluorescent signal of the first channel from the blinking fluorescent signal of the second channel by a beam-splitting system of the two-color fluorescence localized super-resolution microscope, and imaging at different areas of the photosensitive element of the camera respectively;

acquiring all images collected by the camera, determining and recording central coordinates of Airy disks of all fluorescent molecules in the images through Gaussian fitting; and constructing super-resolution image of the first biological structure corresponding to the blinking fluorescent signal of the first channel and super-resolution image of the second biological structure corresponding to the blinking fluorescent signal of the second channel respectively according to the recorded central coordinates of Airy disks.

According to the method of the invention, the two-color fluorescence localized super-resolution microscope is an inverted total internal reflection fluorescence microscope;

the camera is an EMCCD camera; and/or the beam-splitting system comprises a rectangular aperture, a two-color reflector and two filters.

The invention further provides a two-color fluorescence localized super-resolution biological microscopy system which comprises:

a sample labeling module for performing two-color fluorescence labeling on a biological sample by using Alexa647 and Alexa750 fluorescent molecules or Cy5 and Cy7 fluorescent molecules, and soaking the biological sample in an imaging buffer solution;

a signal generation module for illuminating the biological sample by laser to generate a blinking fluorescent signal of a first channel corresponding to the Alexa647 or Cy5 fluorescent molecules as well as a blinking fluorescent signal of a second channel corresponding to the Alexa750 or Cy7 fluorescent molecules respectively;

a first image construction module for constructing a super-resolution image of a first biological structure and a super-resolution image of a second biological structure respectively according to the blinking fluorescent signal of the first channel and the blinking fluorescent signal of the second channel; and a second image construction module for aligning the super-resolution image of the first biological structure and the super-resolution image of the second biological structure to construct a super-resolution image of a third biological structure.

According to the system of the invention, the signal generation module is used for illuminating the biological sample by the specified activation laser to activate a fluorescent signal, and illuminating the biological sample by the specified excitation laser to deactivate the fluorescent signal so as to generate a blinking fluorescent signal.

According to the system of the invention, the activation laser has violet or ultraviolet wavelength; the excitation laser has an excitation wavelength of the Alexa647 and Alexa750 fluorescent molecules, or the excitation laser has an excitation wavelength of the Cy5 and Cy7 fluorescent molecules;

the signal generation module is used for making most fluorescent molecules disable fluorescent signals at the same time at the specified excitation laser power and activation laser power, leaving a small number of discrete fluorescent molecules to activate fluorescent signals.

According to the system of the invention, the imaging buffer solution comprises TCEP, cyclooctatetraene, deoxidant, methyl viologen and/or ascorbic acid; or the imaging buffer solution comprises Thiol, cyclooctatetraene, deoxidant, methyl viologen and/or ascorbic acid.

According to the system of the invention, the TCEP or Thiol and the fluorescent molecules are combined to form an adduct under illumination of the excitation laser, the adduct does not fluoresce under illumination of the excitation laser, the adduct is redecomposed into the TCEP or Thiol and the fluorescent molecules under illumination of the activation laser, and the fluorescent molecules fluoresce.

According to the system of the invention, the cyclooctatetraene comprises derivatives thereof, the deoxidant comprises a combination of glucose oxidase, glucose and catalase, or the deoxidant comprises a combination of pyranose oxidase, glucose and catalase.

According to the system of the invention, the system further comprises:

a real-time locking module for locking the location of the biological sample in real time by a real-time locking system before data acquisition.

According to the system of the invention, the real-time locking module comprises:

a wide-field illumination submodule for providing wide-field illumination for the biological sample, and imaging a wide-field image of the biological sample in a locking camera through front imaging lens;

a module generation submodule for capturing a wide-field image of the biological sample or reference object from the locking camera as a locking template;

an image comparison submodule for capturing a current wide-field image of the biological sample in real time from the locking camera, and comparing the current wide-field image with the locking template;

an offset calculation submodule for computing offset between the current wide-field image and the locking template; and an offset compensation submodule for performing offset compensation on the current wide-field image according to the offset.

According to the system of the invention, the first image construction module further comprises:

a signal acquisition submodule for acquiring the blinking fluorescent signal of first channel and the blinking fluorescent signal of the second channel by a two-color fluorescence localized super-resolution microscope;

a signal separation submodule for separating the blinking fluorescent signal of the first channel from the blinking fluorescent signal of the second channel by a beam-splitting system of the two-color fluorescence localized super-resolution microscope, and imaging at different areas of a photosensitive element of the camera respectively;

a location recording submodule for acquiring all images collected by the camera, determining and recording Airy disk central coordinates of all fluorescent molecules in the images through Gaussian fitting; and an image generation submodule for constructing a super-resolution image of a first biological structure corresponding to the blinking fluorescent signal of the first channel and a super-resolution image of a second biological structure corresponding to the blinking fluorescent signal of the second channel respectively according to the recorded Airy disk central coordinates.

According to the system of the invention, the two-color fluorescence localized super-resolution microscope is an inverted total internal reflection fluorescence microscope;

the camera is an EMCCD camera; and/or the beam-splitting system comprises a rectangular aperture, a two-color reflector and two filters.

The two-color fluorescence localized super-resolution microscopy of the invention uses Alexa647 and Alexa750 fluorescent molecules or Cy5 and Cy7 fluorescent molecules to perform two-color fluorescence labeling on a biological sample. The emission spectra of the used fluorescent molecules are completely separated, as a result, channel crosstalk cannot occur in theory. Furthermore, the excitation wavelength of the fluorescent molecules cannot make the cells fluoresce spontaneously, which greatly reduces the background noise, improves imaging quality and facilitates operation. Preferably, the invention uses optimized imaging buffer solution, which significantly reduces photo-bleaching of florescent molecules in the imaging process. More preferably, in the invention, the sample is locked by the real-time locking function so as to thoroughly eliminate any sample drift in the imaging processing. The invention can be widely applied in the field of bio-optical super-resolution microscopy.

DETAILED DESCRIPTION

In order to make the purpose, technical solution and advantages of the invention more clear, the invention will be described in detail in combination with accompanied drawings and embodiments. It should be understood that various embodiments described herein are only used to explain the invention rather than defining the invention.

Figure 1:
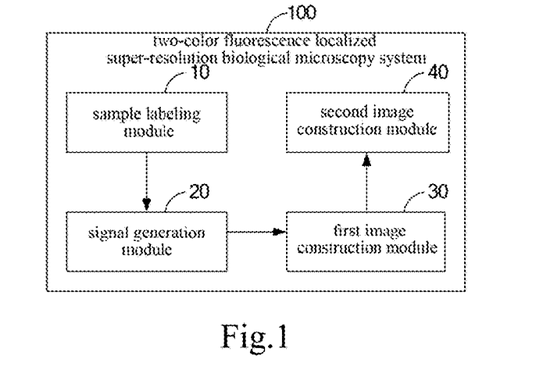
FIG. 1 is a structural diagram of the two-color fluorescence localized super-resolution biological microscopy system of the invention.

FIG. 1 is a structural diagram of the two-color fluorescence localized super-resolution biological microscopy system of the invention. The system 100 comprises a sample labeling module 10, a signal generation module 20, a first image construction module 30 and a second image construction module 40, wherein:

the sample labeling module 10 is used for performing two-color fluorescence labeling on a biological sample by using Alexa647 and Alexa750 fluorescent molecules or Cy5 and Cy7 fluorescent molecules, and soaking the labeled biological sample in an imaging buffer solution. In one embodiment, the Alexa647 and Alexa750 fluorescent molecules are combined on proteins of the biological sample with different structures respectively by an immuno-labelling method, the biological sample is prepared into a sealing sheet and soaked in the imaging buffer solution, and the imaging buffer solution with biological sample soaked is placed on a stage of a two-color fluorescence localized super-resolution microscope. The Alexa647 and Alexa750 fluorescent molecules are preferably taken as the fluorescent molecules of the invention, and can be substituted with anthocyanin dye molecules with the same excitation wavelength, such as Cy5 and Cy7.

The signal generation module 20 is used for illuminating the biological sample by laser to generate a blinking fluorescent signal of a first channel corresponding to the Alexa647 or Cy5 fluorescent molecules as well as a blinking fluorescent signal of a second channel corresponding to the Alexa750 or Cy7 fluorescent molecules respectively. If the Alexa647 and Alexa750 fluorescent molecules are used in the invention, the blinking fluorescent signal of the first channel corresponding to the Alexa647 fluorescent molecules and the blinking fluorescent signal of the second channel corresponding to the Alexa750 fluorescent molecules are generated. If the Cy5 and Cy7 fluorescent molecules are used in the invention, the blinking fluorescent signal of the first channel corresponding to the Cy5 fluorescent molecules and the blinking fluorescent signal of the second channel corresponding to the Cy7 fluorescent molecules are generated.

The first image construction module 30 is used for constructing a super-resolution image of a first biological structure and a super-resolution image of a second biological structure respectively according to the blinking fluorescent signal of the first channel and the blinking fluorescent signal of the second channel.

The second image construction module 40 is used for aligning the super-resolution image of the first biological structure and the super-resolution image of the second biological structure to construct a super-resolution image of a third biological structure.

Preferably, the components of the imaging buffer solution mainly comprise TCEP (tri(2-carboxyethyl) phosphine), COT (cyclooctatetraene), deoxidant, methyl viologen and/or ascorbic acid; or the components of the imaging buffer solution mainly comprise Thiol, COT, deoxidant, methyl viologen and/or ascorbic acid.

The TCEP or Thiol component in the imaging buffer solution and the fluorescent molecules are combined into adduct under the illumination of the excitation laser. The adduct cannot fluoresce under the illumination of the excitation laser, as a result, the fluorescent molecules are closed; the adduct is re-decomposed into TCEP or Thiol and fluorescent molecules under the illumination of the excitation laser, the fluorescent molecules fluoresce and are opened accordingly.

Figure 2:
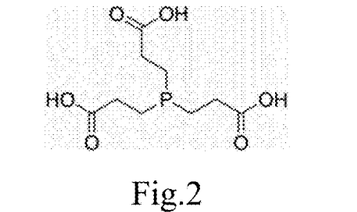
FIG. 2 is a molecular structural diagram of TCEP of the invention.
Figure 3:
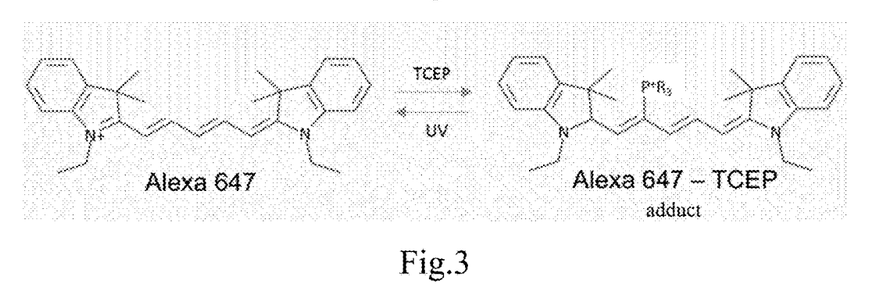
FIG. 3 is a schematic diagram showing fluorescent molecules reacting with TCEP component in an imaging buffer solution in an embodiment of the invention.

FIG. 2 illustrates the molecular structure of TCEP. The Alexa647 fluorescent molecules react with the TCEP component in the imaging buffer solution to generate the adduct as shown in FIG. 3. The Alexa647 fluorescent molecules shown in FIG. 3 are taken as an example for detailed description only. Such principle is applicable to anthocyanin fluorescent molecules including Alexa750, Cy5 and Cy7.

Figure 4:
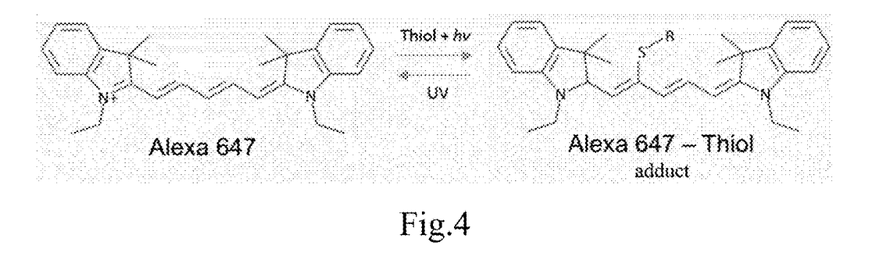
FIG. 4 is a schematic diagram showing fluorescent molecules reacting with Thiol component in the imaging buffer solution in an embodiment of the invention.

The Alexa647 fluorescent molecules react with the Thiol component in the imaging buffer solution to generate the adduct as shown in FIG. 4. The Alexa647 fluorescent molecules shown in FIG. 4 are taken as an example for detailed description only. Such principle is applicable to anthocyanin fluorescent molecules including Alexa750, Cy5 and Cy7.

The Thiol comprise βME (2-mercaptoethanol), or MEA (ethanolamine), etc. However, the Thiol could possibly reduce the photon number of the Alexa750 molecules, and increase the photo-bleaching probability of the fluorescent molecules, affecting the image quality.

The COT in the imaging buffer solution comprises COT derivative. The COT of the invention is dissolved in DMSO (dimethyl sulfoxide). The COT in the imaging buffer solution can inhibit the fluorescent molecules to enter triplet state in an atmosphere of lacking oxygen molecules, thus improving the number of photons generated by the fluorescent molecules in open status and improving the resolution, simultaneously reducing the photo-bleaching probability of the fluorescent molecules and improving the imaging quality.

The deoxidant comprises a combination of glucose oxidase, glucose and catalase; or the deoxidant comprises a combination of pyranose oxidase, glucose and catalase. The combination of glucose oxidase (or pyranose oxidase), glucose and catalase in the imaging buffer solution can remove oxygen from the buffer solution, greatly reduce the photo-bleaching probability of the fluorescent molecules and improve the imaging quality. The invention is not limited to use the combination of glucose oxidase (or pyranose oxidase), glucose and catalase as the deoxidant. Other feasible deoxidization solution also can be used in the invention.

As reducing agents, the methyl viologen and ascorbic acid in the imaging buffer solution can inhibit photo-blenching of the fluorescent molecules.

More than 2000 photons will be generated in every luminescence cycle of the fluorescent molecules owing to the optimized imaging buffer solution formula of the invention, and the deoxidant and COT component in the imaging buffer solution greatly reduce the photo-bleaching of photons, thus generating high quality two-color super-resolution images. The lateral resolution of the Alexa647 channel can be up to 10 nm under ideal condition, and that of the Alexa750 channel can be up to 20 nm.

In Example 1, the imaging buffer solution mainly consists of 200 mM Tris phosphate buffer solution, pH 9.0; 10% (w/v) glucose, 5 U/ml pyranose oxidase, 57 μg/ml catalase, 2 mM COT (dissolved in DMSO), 25 mM TCEP, 1 mM ascorbic acid and 1 mM methyl viologen.

In Example 2, the imaging buffer solution mainly consists of 200 mM Tris phosphate buffer solution, pH 8.0; 10% (w/v) glucose, 560 μg/ml glucose oxidase, 57 μg/ml catalase, 2 mM COT (dissolved in DMSO), 25 mM TCEP, 1 mM ascorbic acid and 1 mM methyl viologen.

Preferably, the signal generation module 20 is used for illuminating the biological sample by the specified activation laser to activate a fluorescent signal, and illuminating the biological sample by the specified excitation laser to deactivate the fluorescent signal so as to generate a blinking fluorescent signal. The activation laser has a violet or ultraviolet wavelength. The excitation laser has excitation wavelength of the Alexa647 and Alexa750 fluorescent molecules, or excitation wavelength of the Cy5 and Cy7 fluorescent molecules. The signal generation module 20 is used for making most fluorescent molecules deactivate fluorescent signals at the same time at the specified excitation laser power and activation laser power, leaving a small number of discrete fluorescent molecules to activate fluorescent signals.

In one embodiment, the packaged biological sample is placed on a stage of an inverted microscope, 656.5 nm laser with output power of 300 mW and 750 nm laser with output power of 300 mW are used to irradiate the sample by total internal reflection mode.

The emission spectra of the Alexa647 and Alexa750 fluorescent molecules or the Cy5 and Cy7 fluorescent molecules are completely separated in the invention, as a result, channel crosstalk will not occur in theory. In addition, the excitation wavelength of the fluorescent molecules used in the invention will not make the cells generate autofluorescence, thus greatly reducing the background noise.

Figure 5:
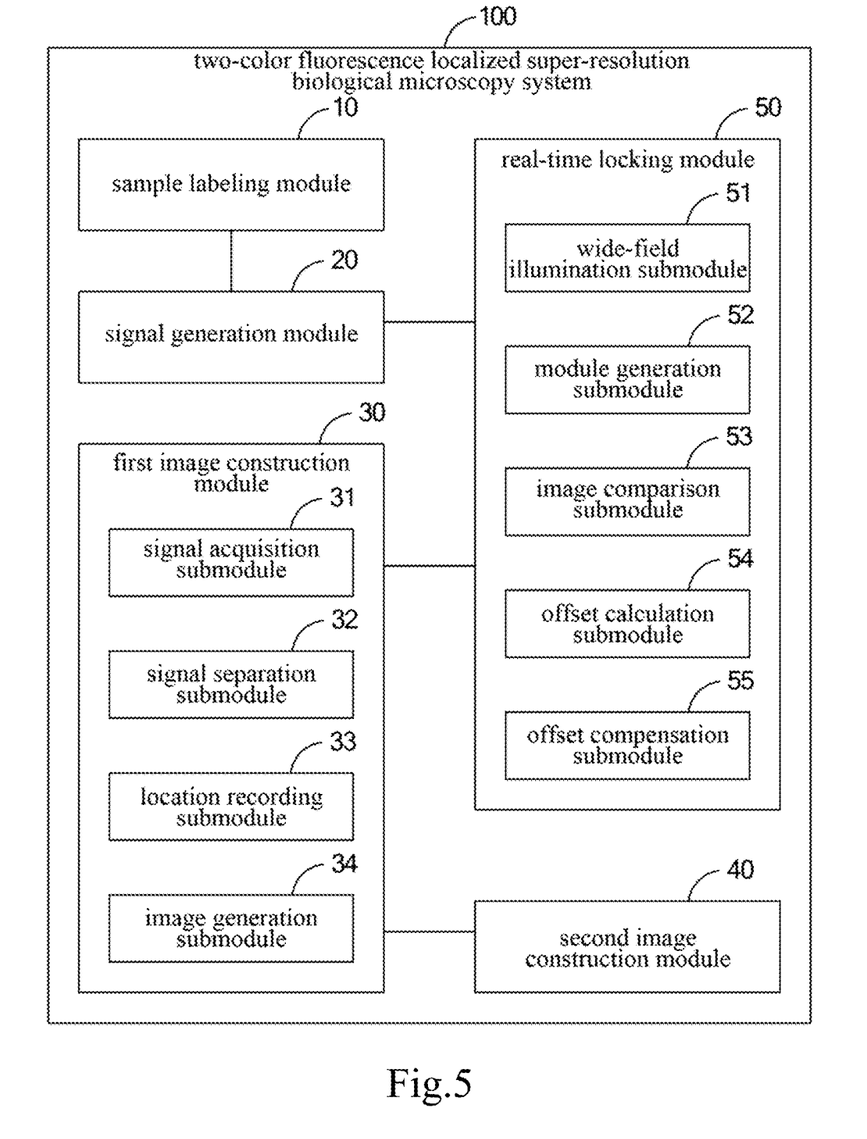
FIG. 5 is a structural diagram of the preferred two-color fluorescence localized super-resolution biological microscopy system of the invention.

FIG. 5 is a structural diagram of the preferred two-color fluorescence localized super-resolution biological microscopy system of the invention. The system 100 comprises a sample labeling module 10, a signal generation module 20, a first image construction module 30, a second image construction module 40 and a real-time locking module 50, wherein:

the sample labeling module 10 is used for performing two-color fluorescence labeling on a biological sample by using Alexa647 and Alexa750 fluorescent molecules or Cy5 and Cy7 fluorescent molecules, and soaking the labeled biological sample in an imaging buffer solution.

The signal generation module 20 is used for illuminating the biological sample by laser to generate a blinking fluorescent signal of a first channel corresponding to the Alexa647 or Cy5 fluorescent molecules as well as a blinking fluorescent signal of a second channel corresponding to the Alexa750 or Cy7 fluorescent molecules respectively.

The biological sample is illuminated by the specified activation laser to activate a fluorescent signal, and the biological sample is illuminated by the specified excitation laser to deactivate the fluorescent signal so as to generate a blinking fluorescent signal, and illuminating the biological sample by the excitation laser of Alexa647 and Alexa750 to generate the fluorescent signal at the same time. Under the action of the imaging buffer solution, the fluorescent molecules are randomly opened (fluoresces) or closed (not fluoresce) to flash after being illuminated by strong excitation laser. The activation speed of the fluorescent molecules of the invention can be controlled by the activation laser beam in milliwatt. The activation speed is proportional to the activation laser power. The closing speed of the fluorescent molecules can be controlled by the intensity of the excitation laser thereof. The closing speed is proportional to the intensity of the excitation laser. The excitation laser is generated by a laser at the excitation wavelength of Alexa647 molecules and a laser having the excitation wavelength of Alexa750 molecules; and the activation laser is generated by a laser having violet or ultraviolet wavelength. The invention uses appropriate excitation laser power and activation laser power to make most fluorescent molecules in closed status at the same time, leaving a small number of discrete fluorescent molecules in open status. The formed images of these opened fluorescent molecules do not overlap.

The real-time locking module 50 is used for locking the position of the biological sample in real time by a real-time locking system before data acquisition to thoroughly remove sample drift during imaging. Preferably, the real-time locking module 50 comprises:

a wide-field illumination submodule 51 for providing wide-field illumination for the biological sample, and imaging a wide-field image of the biological sample in a locking camera through front imaging lens;

a module generation submodule 52 for capturing a wide-field image of the biological sample or reference object from the locking camera as a locking template;

an image comparison submodule 53 for capturing a current wide-field image of the biological sample in real time from the locking camera, and comparing the current wide-field image with the locking template;

an offset calculation submodule 54 for computing offset between the current wide-field image and the locking template; Specifically, the offset of the biological sample can be obtained by correlation operation or normalized cross-correlation operation.

an offset compensation submodule 55 for performing offset compensation on the current wide-field image according to the offset. The process is cycled until shooting is ended.

In the real-time sample locking method used in the invention, the position of the biological sample can be locked at nanometer precision without adding any fluorescent marker, to eliminate sample drift during shooting process and further improve imaging resolution of the system. The wide-field image of the biological sample is taken as a locking reference, and locking accuracy is reduced; as the wide-field image is different from fluorescent particles and does not cause photo-bleaching during long-time data acquisition process. The real-time sample locking method used in the invention can lock cells for a long time. When the biological sample taken is too small or thin to generate a wide-field image with high signal to noise ratio, a small quantity of 1.2 micro-diameter polystyrene microspheres and other reference objects can be adhered to the glass slide to generate a wide-field image, which can substitute the biological sample as a lock target.

The first image construction module 30 is used for constructing a super-resolution image of a first biological structure and a super-resolution image of a second biological structure respectively according to the blinking fluorescent signal of the first channel and the blinking fluorescent signal of the second channel.

The second image construction module 40 is used for aligning the super-resolution image of the first biological structure and the super-resolution image of the second biological structure to construct a super-resolution image of a third biological structure.

Preferably, the first image construction module 30 also comprises:

a signal acquisition submodule 31 for acquiring the blinking fluorescent signal of the first channel and the blinking fluorescent signal of the second channel by a two-color fluorescence localized super-resolution microscope. Preferably, the two-color fluorescence localized super-resolution microscope is a total internal reflection fluorescence microscope (TIRFM), i.e. the channel blinking fluorescent signal is received by the inverted TIRFM.

a signal separation submodule 32 for separating the blinking fluorescent signal of the first channel from the blinking fluorescent signal of the second channel by a beam-splitting system of the two-color fluorescence localized super-resolution microscope, and imaging at different areas of a photosensitive element of the camera respectively. Preferably, the camera is electron-multiplying charge-coupled device (EMCCD) camera and the beam-splitting system comprises a rectangular aperture, a two-color reflector and two filters. The fluorescent signal from dye molecules is received by the microscope, separated by the beam-splitting system and imaged at different areas of the photosensitive element of the EMCCD camera. The appropriate excitation laser power and activation laser power are used to make most fluorescent molecules in closed status at the same time, leaving a small number of discrete fluorescent molecules in open status. The formed images of these opened fluorescent molecules do not overlap.

a location recording submodule 33 for acquiring all images collected by the camera, determining and recording Airy disk central coordinates of all fluorescent molecules in the images through Gaussian fitting. Due to optical resolution limit, the formed image of each fluorescent molecule is an Airy Disk. The locating software acquires the images from EMCCD camera and determines all Airy disk central coordinates through Gaussian fitting. These coordinates accurately represent the actual locations of fluorescent molecules and are recorded by program. The EMCCD camera records blinking fluorescent signal at high speed until almost all fluorescent molecules are located and recorded.

an image generation submodule 34 for constructing a super-resolution image of a first biological structure corresponding to the blinking fluorescent signal of the first channel and a super-resolution image of a second biological structure corresponding to the blinking fluorescent signal of the second channel respectively according to the recorded Airy disk central coordinates. The program reconstructs the super-resolution biological structure images corresponding to all channels respectively according to the Airy disk central coordinates determined through Gaussian fitting.

The invention provides a two-color fluorescence localized super-resolution microscopy system based on Alexa647 and Alexa750 fluorescent molecular marking. Meanwhile, the microscopy system is capable of implementing a cell locking function to eliminate sample drift. The microscopy system has simple structure and can operate easily. The application of the optimized imaging buffer solution greatly reduces photo-bleaching of fluorescent molecules during imaging process and eliminates channel crosstalk. The sample is directly locked by the wide-field image of cells to eliminate any sample drift during the imaging process. The invention can be widely applied in the field of bio-optical super-resolution microscopy.

Figure 6:
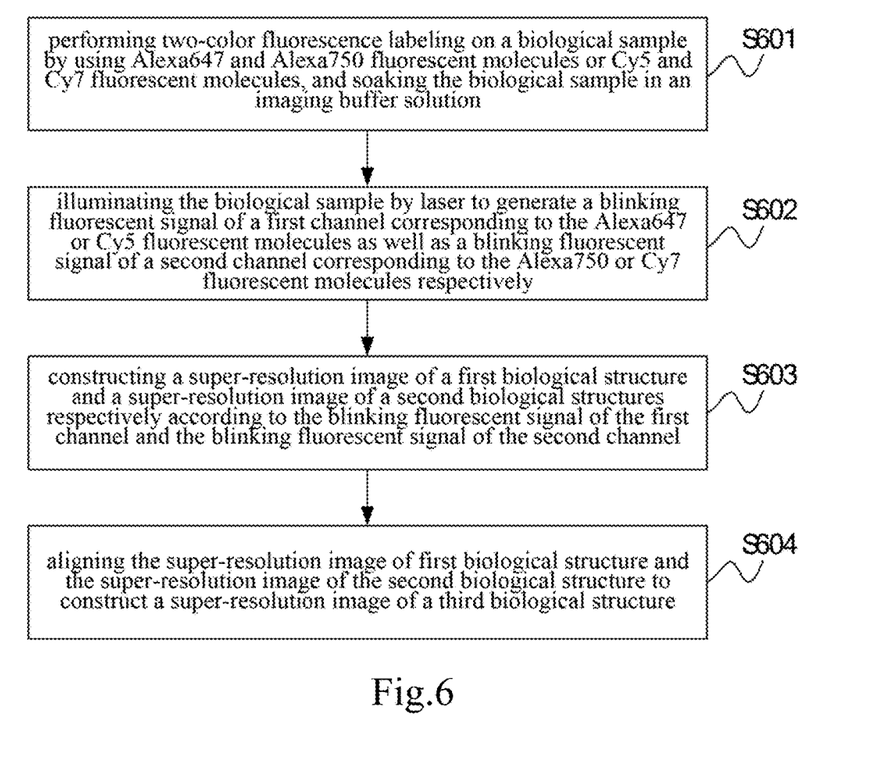
FIG. 6 is a flow chart of the two-color fluorescence localized super-resolution biological microscopy method of the invention.

FIG. 6 is a flow chart of the two-color fluorescence localized super-resolution biological microscopy method of the invention, which can be implemented by the system 100 shown in FIG. 1 or FIG. 4, and comprises step S601, performing two-color fluorescence labeling on a biological sample by using Alexa647 and Alexa750 fluorescent molecules or Cy5 and Cy7 fluorescent molecules, and soaking the biological sample in an imaging buffer solution.

In one embodiment, the Alexa647 and Alexa750 fluorescent molecules are combined on proteins of the biological sample with different structures respectively by an immuno-labelling method, the biological sample is prepared into a sealing sheet and soaked in the imaging buffer solution, and the imaging buffer solution with biological sample soaked is placed on a stage of a two-color fluorescence localized super-resolution microscope. The Alexa647 and Alexa750 fluorescent molecules are preferably taken as the fluorescent molecules of the invention, and can be substituted with anthocyanin dye molecules with the same excitation wavelength, such as Cy5 and Cy7.

step S602, illuminating the biological sample by laser to generate a blinking fluorescent signal of a first channel corresponding to the Alexa647 or Cy5 fluorescent molecules as well as a blinking fluorescent signal of a second channel corresponding to the Alexa750 or Cy7 fluorescent molecules respectively.

If the Alexa647 and Alexa750 fluorescent molecules are used in the invention, the 1 blinking fluorescent signal of the first channel corresponding to the Alexa647 fluorescent molecules and the blinking fluorescent signal of the second channel corresponding to the Alexa750 fluorescent molecules are generated. If the Cy5 and Cy7 fluorescent molecules are used in the invention, the blinking fluorescent signal of the first channel corresponding to the Cy5 fluorescent molecules and the blinking fluorescent signal of the second channel corresponding to the Cy7 fluorescent molecules are generated.

Preferably, the biological sample is illuminated by the specified activation laser to activate a fluorescent signal, and the biological sample is illuminated by the specified excitation laser to deactivate the fluorescent signal so as to generate a blinking fluorescent signal. The activation laser has a violet or ultraviolet wavelength. The excitation laser has an excitation wavelength of the Alexa647 and Alexa750 fluorescent molecules, or the excitation laser has an excitation wavelength of the Cy5 and Cy7 fluorescent molecules. The signal generation module 20 is used for making most fluorescent molecules deactivate fluorescent signals at the same time at the specified excitation laser power and activation laser power, leaving a small number of discrete fluorescent molecules to activate fluorescent signals.

step S603, constructing a super-resolution image of a first biological structure and a super-resolution image of a second biological structure respectively according to the blinking fluorescent signal of the first channel and the blinking fluorescent signal of the second channel.

step S604, aligning the super-resolution image of the first biological structure and the super-resolution image of the second biological structure to construct a super-resolution image of a third biological structure.

Preferably, the components of the imaging buffer solution mainly comprise TCEP (tri(2-carboxyethyl) phosphine), COT (cyclooctatetraene), deoxidant, methyl viologen and/or ascorbic acid; or the components of the imaging buffer solution mainly comprise Thiol, COT, deoxidant, methyl viologen and/or ascorbic acid.

The TCEP or Thiol component in the imaging buffer solution and the fluorescent molecules are combined into an adduct under the illumination of the excitation laser. The adduct cannot fluoresce under the illumination of the excitation laser, as a result, the fluorescent molecules are closed; the adduct is re-decomposed into TCEP or Thiol and fluorescent molecules under the illumination of the excitation laser, the fluorescent molecules fluoresce and are opened accordingly.

FIG. 2 illustrates the molecular structure of TCEP. The Alexa647 fluorescent molecules react with the TCEP component in the imaging buffer solution to generate the adduct as shown in FIG. 3. The Alexa647 fluorescent molecules shown in FIG. 3 are taken as an example for detailed description only. Such principle is applicable to anthocyanin fluorescent molecules including Alexa750, Cy5 and Cy7.

The Alexa647 fluorescent molecules react with the Thiol component in the imaging buffer solution to generate the adduct as shown in FIG. 4. The Alexa647 fluorescent molecules shown in FIG. 4 are taken as an example for detailed description only. Such principle is applicable to anthocyanin fluorescent molecules including Alexa750, Cy5 and Cy7.

The Thiol comprises βME (2-mercaptoethanol), or MEA (ethanolamine), etc. However, the Thiol could possibly reduce the photon number of the Alexa750 molecules, and increase the photo-bleaching probability of the fluorescent molecules, affecting the image quality.

The COT in the imaging buffer solution comprises COT derivative. The COT of the invention is dissolved in DMSO (dimethyl sulfoxide). The COT in the imaging buffer solution can inhibit the fluorescent molecules to enter triplet state, thus improving the number of photons generated by the fluorescent molecules in open status and improving the resolution, simultaneously reducing the photo-bleaching probability of the fluorescent molecules and improving the imaging quality.

The deoxidant comprises a combination of glucose oxidase, glucose and catalase; or the deoxidant comprises a combination of pyranose oxidase, glucose and catalase. The combination of glucose oxidase (or pyranose oxidase), glucose and catalase in the imaging buffer solution can remove oxygen from the buffer solution, greatly reduce the photo-bleaching probability of the fluorescent molecules and improve the imaging quality. The invention is not limited to use the combination of glucose oxidase (or pyranose oxidase), glucose and catalase as the deoxidant. Other feasible deoxidization solution also can be used in the invention.

The methyl viologen and ascorbic acid in the imaging buffer solution can be taken as reducing agents to inhibit photo-blenching of the fluorescent molecules.

In one embodiment, the packaged biological sample is placed on a stage of an inverted microscope, 656.5 nm laser with output power of 300 mW and 750 nm laser with output power of 300 mW are used to irradiate the sample by total internal reflection mode.

Figure 7:
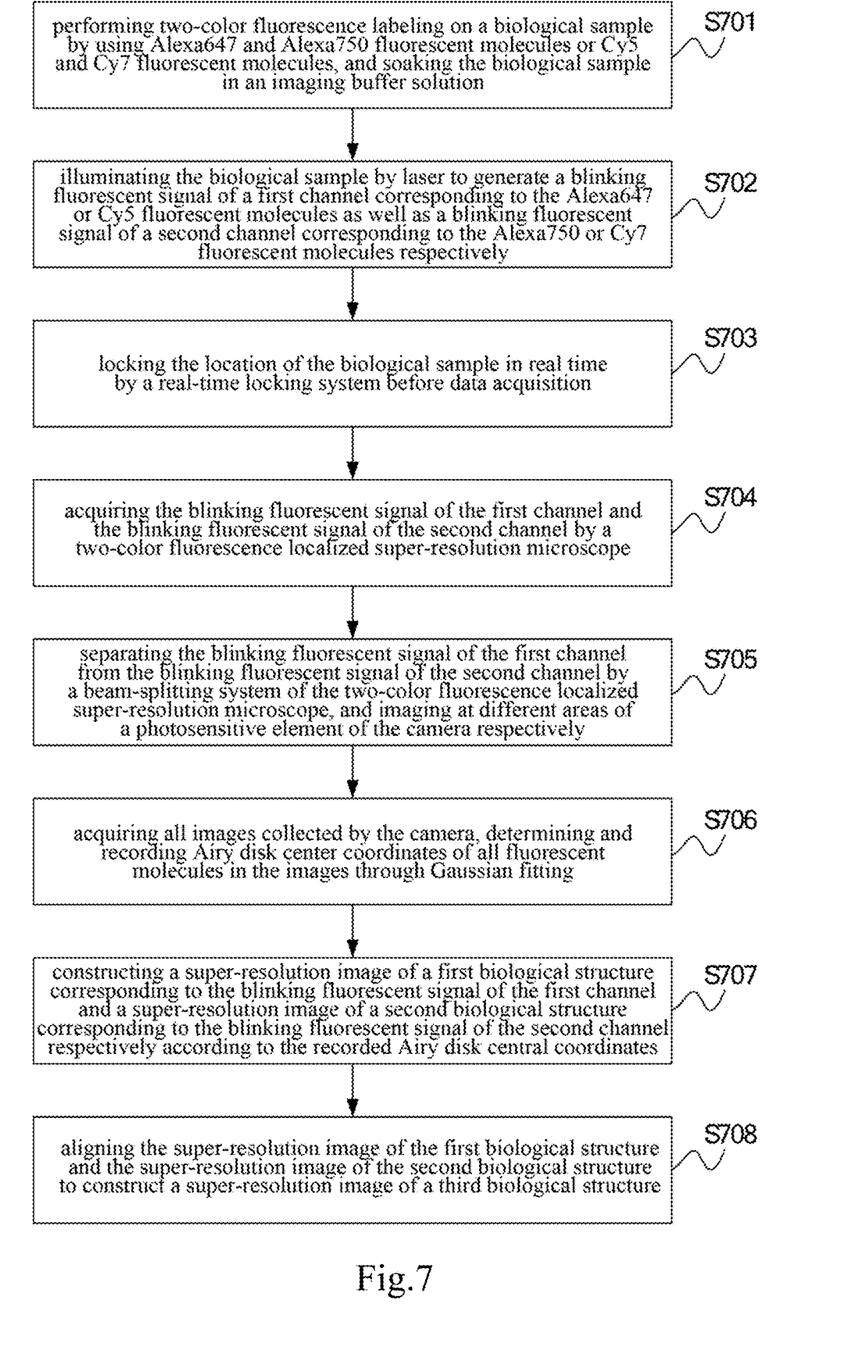
FIG. 7 is a flow chart of the preferred two-color fluorescence localized super-resolution biological microscopy method of the invention.

FIG. 7 is a flow chart of the preferred two-color fluorescence localized super-resolution biological microscopy method of the invention, which can be implemented by the system 100 shown in FIG. 4, and comprises:

Step S701: performing two-color fluorescence labeling on a biological sample by using Alexa647 and Alexa750 fluorescent molecules or Cy5 and Cy7 fluorescent molecules, and soaking the biological sample in an imaging buffer solution.

Preferably, in the two-color fluorescence super-resolution microscopy method involved in the invention, the Alexa647 and Alexa750 fluorescent molecules are used to label specific structure of the biological sample by immune response, and the biological sample is soaked in the imaging buffer solution containing TCEP.

Step S702: illuminating the biological sample by laser to generate a blinking fluorescent signal of a first channel corresponding to the Alexa647 or Cy5 fluorescent molecules as well as a blinking fluorescent signal of a second channel corresponding to the Alexa750 or Cy7 fluorescent molecules respectively.

The biological sample is illuminated by the specified activation laser to activate a fluorescent signal, and the biological sample is illuminated by the specified excitation laser to deactivate the fluorescent signal so as to generate a blinking fluorescent signal. The activation speed of the fluorescent molecules of the invention can be controlled by the activation laser beam in milliwatt. The activation speed is proportional to the activation laser power. The closing speed of the fluorescent molecules can be controlled by the intensity of the excitation laser thereof. The closing speed is proportional to the intensity of the excitation laser. The excitation laser is generated by a laser at the excitation wavelength of Alexa647 molecules and a laser at the excitation wavelength of Alexa750 molecules; and the activation laser is generated by a laser having violet or ultraviolet wavelength. The invention uses appropriate excitation laser power and activation laser power to make most fluorescent molecules in closed status at the same time, leaving a small number of discrete molecules in open status. The formed images of these opened fluorescent molecules do not overlap.

Step S703: locking the location of the biological sample in real time by a real-time locking system before data acquisition. The step further comprises:

providing wide-field illumination for the biological sample, and imaging a wide-field image of the biological sample in a locking camera through front imaging lens;

capturing a wide-field image of the biological sample or reference object from the locking camera as a locking template;

capturing a current wide-field image of the biological sample in real time from the locking camera, and comparing the current wide-field image with the locking template;

computing offset between the current wide-field image and the locking template; and performing offset compensation processing on the current wide-field image according to the offset, and cycling the process to the end of shooting.

Step S704: acquiring the blinking fluorescent signal of the first channel and the blinking fluorescent signal of the second channel by a two-color fluorescence localized super-resolution microscope.

Preferably, the two-color fluorescence localized super-resolution microscope is an inverted total internal reflection fluorescence microscope.

Step S705: separating the blinking fluorescent signal of the first channel from the blinking fluorescent signal of the second channel by a beam-splitting system of the two-color fluorescence localized super-resolution microscope, and imaging at different areas of a photosensitive element of the camera respectively.

Preferably, the camera is an electron-multiplying charge-coupled device (EMCCD) camera, and the beam-splitting system comprises a rectangular aperture, a two-color reflector and two filters. The fluorescent signal from dye molecules is received by the microscope, separated by the beam-splitting system and imaged at different areas of a photosensitive element of the EMCCD camera. Appropriate excitation laser power and activation laser power are used to make most fluorescent molecules in closed status at the same time, leaving a small number of discrete molecules in open status. The formed images of these opened fluorescent molecules do not overlap.

Step S706: acquiring all images collected by the camera, determining and recording Airy disk central coordinates of all fluorescent molecules in the images through Gaussian fitting.

Due to optical resolution limit, the formed image of each fluorescent molecule is an Airy Disk. The locating software acquires the images from EMCCD camera and determines all Airy disk central coordinates through Gaussian fitting. These coordinates accurately represent the actual locations of fluorescent molecules and are recorded by program. The EMCCD camera records the blinking fluorescent signals at a high speed to locate and record almost all of these fluorescent molecules.

Step S707: constructing a super-resolution image of a first biological structure corresponding to the blinking fluorescent signal of the first channel and a super-resolution image of a second biological structure corresponding to the blinking fluorescent signal of the second channel respectively according to the recorded Airy disk central coordinates.

The program reconstructs the super-resolution biological structure images corresponding to all channels respectively according to the Airy disk central coordinates determined through Gaussian fitting.

Step S708: aligning the super-resolution image of the first biological structure and the super-resolution image of the second biological structure to construct a super-resolution image of a third biological structure.

Figure 8:
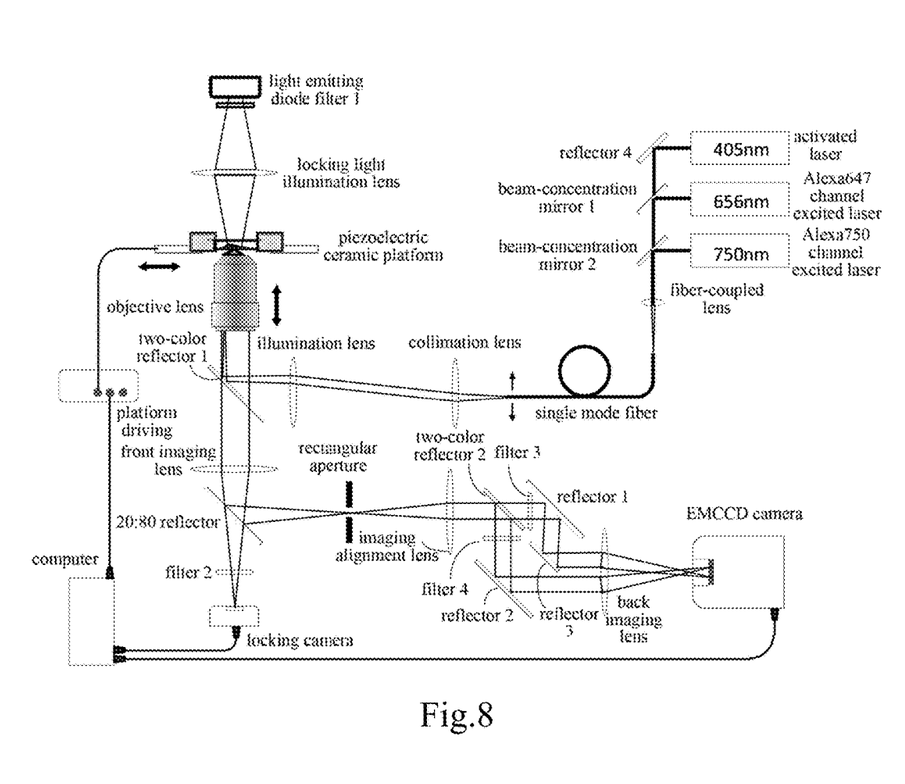
FIG. 8 is a structural diagram of the two-color fluorescence localized super-resolution biological microscopy system in an embodiment of the invention.

FIG. 8 is a structural diagram of the two-color fluorescence localized super-resolution biological microscopy system in an embodiment of the invention, comprising an optical structure diagram of a real-time cell locking system.

Firstly, the invention thoroughly removes any sample drift in the imaging processing through the real-time cell locking system. The principle comprises: 1) providing wide-field illumination for the sample by using the blue light generated by a light emitting diode and filter 1 in FIG. 8; 2) imaging a wide-field image of the sample in a locking camera through front imaging lens; 3) when starting up the locking program in a computer, capturing a template image of the sample from the locking camera by the program as a locking template; 4) capturing a wide-field image of the sample in real time from the locking camera by the locking system, and comparing the wide-field image with the locking template through related algorithm; 5) obtaining the offset between the current image and the locking template through related algorithm; 6) compensating the offset by driving the piezoelectric ceramic platform through drive circuit by the locking program; and 7) cycling the process to the end of shooting.

The detection optical path of the invention is shown in FIG. 8. The blinking fluorescent signals sent from fluorescence label on the sample are received by 100× objective lens. The fluorescent signal comprises: channel 1: fluorescence from Alexa647 molecules; and channel 2: fluorescence from Alexa758 molecules. The signals of these two channels are separated by the beam-splitting system comprising a rectangular aperture, a two-color reflector 2, a filter 3 and a filter 4, and imaged at different areas of a photosensitive element of the EMCCD camera respectively. The EMCCD camera records the blinking fluorescent point signals from both channels simultaneously in video recording mode. The locating software acquires all images collected by the EMCCD camera, and determines and records all Airy disk central coordinates of all images through Gaussian fitting. Subsequently, the program depicts the recorded central coordinates as points to reconstruct the super-resolution biological structure images of Alexa647 and Alexa750 channels respectively. Finally, the images of both channels are accurately aligned through an algorithm to obtain the two-color fluorescence super-resolution micrograph of the labeled sample.

To sum up, the two-color fluorescence localized super-resolution microscopy of the invention performs two-color fluorescence labeling on a biological sample by using Alexa647 and Alexa750 fluorescent molecules or Cy5 and Cy7 fluorescent molecules. The emission spectra of the used fluorescent molecules are completely separated. As a result, channel crosstalk cannot occur in theory. In addition, the excitation wavelength of the fluorescent molecules cannot make the cells autofluorescence, which significantly reduces the background noise, improves imaging quality and facilitates operation. Preferably, the invention uses optimized imaging buffer solution, which significantly reduces photobleaching of florescent molecules in the imaging process. More preferably, in the invention, the sample is locked by the real-time locking function so as to thoroughly eliminate any sample drift in the imaging processing. The invention can be widely applied in the field of bio-optical super-resolution microscopy.

The invention should not be restricted to the specifically described embodiments thereof. Any changes and modifications made based on the spirit and essence of the invention can be incorporated in the protection scope of the claims appended to the invention.

The invention claimed is:

1. A two-color fluorescence localized super-resolution biological microscopy method, comprising the following steps:
    performing two-color fluorescence labeling on a biological sample by using Alexa647 and Alexa750 fluorescent molecules or Cy5 and Cy7 fluorescent molecules, and soaking the biological sample in an imaging buffer solution comprising TCEP (tri(2-carboxyethyl) phosphine and/or Thiol;
    illuminating the biological sample by laser to generate a blinking fluorescent signal of a first channel corresponding to the Alexa647 or Cy5 fluorescent molecules as well as a blinking fluorescent signal of a second channel corresponding to the Alexa750 or Cy7 fluorescent molecules respectively;
    constructing a super-resolution image of a first biological structure and a super-resolution image of a second biological structure respectively according to the blinking fluorescent signal of the first channel and the blinking fluorescent signal of the second channel; and
    aligning the super-resolution image of the first biological structure and the super-resolution image of the second biological structure to construct a super-resolution image of a third biological structure;
    wherein the step of illuminating the biological sample comprises:
    1) illuminating the biological sample by an activation laser, and thereby activating a fluorescent signal, and
    2) illuminating the biological sample by an excitation laser, and thereby deactivating the fluorescent signal and generating the blinking fluorescent signals; and
    wherein the TCEP or Thiol and the fluorescent molecules form an adduct under illumination of the excitation laser, the adduct does not fluoresce under illumination of the excitation laser, and wherein the adduct is redecomposed into the TCEP or Thiol and the fluorescent molecules fluoresce under illumination of the activation laser.

2. The method according to claim 1, characterized in that the activation laser has a violet or ultraviolet wavelength; the excitation laser has an excitation wavelength of the Alexa647 and Alexa750 fluorescent molecules, or the excitation laser has excitation wavelength of the Cy5 and Cy7 fluorescent molecules; and the specified excitation laser power and activation laser power are used to allow most fluorescent molecules to deactivate fluorescent signals at the same time, leaving a small number of discrete fluorescent molecules to activate fluorescent signals.

3. The method according to claim 1, characterized in that the imaging buffer solution further comprises cyclooctatetraene, deoxidant, methyl viologen and/or ascorbic acid.

4. The method according to claim 3, characterized in that the cyclooctatetraene comprises derivatives thereof, the deoxidant comprises a combination of glucose oxidase, glucose and catalase, or the deoxidant comprises a combination of pyranose oxidase, glucose and catalase.

5. The method according to claim 1, characterized by further comprising the following step before the step of constructing a super-resolution image of a first biological structure and a super-resolution image of a second biological structure respectively according to the blinking fluorescent signal of the first channel and the blinking fluorescent signal of the second channel;
    locking the location of the biological sample in real time by a real-time locking system before data acquisition.

6. The method according to claim 5, characterized in that the step of locking the location of the biological sample in real time by a real-time locking system further comprises the following steps:
    providing wide-field illumination for the biological sample, and imaging a wide-field image of the biological sample in a locking camera through a front imaging lens;
    capturing a wide-field image of the biological sample or reference object from the locking camera as a locking template;
    capturing a current wide-field image of the biological sample in real time from the locking camera, and comparing the current wide-field image with the locking template;
    computing offset between the current wide-field image and the locking template;
    performing offset compensation on the current wide-field image according to the offset.

7. The method according to claim 1, characterized in that the step of constructing a super-resolution image of a first biological structure and a super-resolution image of a second biological structure respectively according to the blinking fluorescent signal of the first channel and the blinking fluorescent signal of the second channel further comprises the following steps:
  acquiring the blinking fluorescent signal of the first channel and the blinking fluorescent signal of the second channel by a two-color fluorescence localized super-resolution microscope;
  separating the blinking fluorescent signal of the first channel from the blinking fluorescent signal of the second channel by a beam-splitting system of the two-color fluorescence localized super-resolution microscope, and imaging at different areas of a photosensitive element of the camera respectively;
  acquiring all images collected by the camera, determining and recording Airy disk central coordinates of all fluorescent molecules in the images through Gaussian fitting; and
  constructing the super-resolution image of the first biological structure corresponding to the blinking fluorescent signal of the first channel and the super-resolution image of the second biological structure corresponding to the blinking fluorescent signal of the second channel respectively according to the Airy disk central coordinates recorded.

8. The method according to claim 7, characterized in that the two-color fluorescence localized super-resolution microscope is an inverted total internal reflection fluorescence microscope;
  the camera is an EMCCD camera; and/or
  the beam-splitting system comprises a rectangular aperture, a two-color reflector and two filters.

9. A two-color fluorescence localized super-resolution biological microscopy system, comprising:
  a sample labeling module for performing two-color fluorescence labeling on a biological sample by using Alexa647 and Alexa750 fluorescent molecules or Cy5 and Cy7 fluorescent molecules, and soaking the biological sample in an imaging buffer solution; wherein the imaging buffer solution comprises TCEP (tri(2-carboxyethyl) phosphine and/or Thiol; and
  wherein the TCEP and/or Thiol and the fluorescent molecules are combined to form an adduct under illumination of the excitation laser, the adduct does not fluoresce under illumination of the excitation laser, the adduct is redecomposed into the TCEP or Thiol and the fluorescent molecules under illumination of the activation laser, and the fluorescent molecules fluoresce;
  a signal generation module for illuminating the biological sample by laser to generate a blinking fluorescent signal of a first channel corresponding to the Alexa647 or Cy5 fluorescent molecules as well as a blinking fluorescent signal of a second channel corresponding to the Alexa750 or Cy7 fluorescent molecules respectively;
  a first image construction module for constructing a super-resolution image of a first biological structure and a super-resolution image of a second biological structure respectively according to the blinking fluorescent signal of the first channel and the blinking fluorescent signal of the second channel; and
  a second image construction module for aligning the super-resolution image of the first biological structure and the super-resolution image of the second biological structure to construct a super-resolution image of a third biological structure.

10. The system according to claim 9, characterized in that the signal generation module is used for illuminating the biological sample by the specified activation laser to activate a fluorescent signal, and illuminating the biological sample by the specified excitation laser to deactivate the fluorescent signal so as to generate the blinking fluorescent signals.

11. The system according to claim 10, characterized in that the activation laser has a violet or ultraviolet wavelength; the excitation laser has excitation wavelength of the Alexa647 and Alexa750 fluorescent molecules, or the excitation laser has an excitation wavelength of the Cy5 and Cy7 fluorescent molecules;
  the signal generation module is used for making most fluorescent molecules deactivate fluorescent signals at the same time at the specified excitation laser power and activation laser power, leaving a small number of discrete fluorescent molecules to activate fluorescent signals.

12. The system according to claim 9, characterized in that the imaging buffer solution further comprises, cyclooctatetraene, deoxidant, methyl viologen and/or ascorbic acid.

13. The system according to claim 12, characterized in that the cyclooctatetraene comprises derivatives thereof, the deoxidant comprises a combination of glucose oxidase, glucose and catalase, or the deoxidant comprises a combination of pyranose oxidase, glucose and catalase.

14. The system according to claim 9, characterized by further comprising:
  a real-time locking module for locking the location of the biological sample in real time by a real-time locking system before data acquisition.

15. The system according to claim 14, characterized in that the real-time locking module comprises:
  a wide-field illumination submodule for providing wide-field illumination for the biological sample, and imaging a wide-field image of the biological sample in a locking camera through front imaging lens;
  a module generation submodule for capturing a wide-field image of the biological sample or reference object from the locking camera as a locking template;
  an image comparison submodule for capturing a current wide-field image of the biological sample in real time from the locking camera, and comparing the current wide-field image with the locking template;
  an offset calculation submodule for computing offset between the current wide-field image and the locking template; and
  an offset compensation submodule for performing offset compensation on the current wide-field image according to the offset.

16. The system according to claim 9, characterized in that the first image construction module further comprises:
  a signal acquisition submodule for acquiring the blinking fluorescent signal of the first channel and the blinking fluorescent signal of the second channel by a two-color fluorescence localized super-resolution microscope;
  a signal separation submodule for separating the blinking fluorescent signal of the first channel from the flashing fluorescent signal of the second channel by a beam-splitting system of the two-color fluorescence localized super-resolution microscope, and imaging at different areas of a photosensitive element of the camera respectively;

a location recording submodule for acquiring all images collected by the camera, determining and recording Airy disk central coordinates of all fluorescent molecules in the images through Gaussian fitting; and an image generation submodule for constructing the super-resolution image of the first biological structure corresponding to the flashing fluorescent signal of the first channel and the super-resolution image of the second biological structure corresponding to the flashing fluorescent signal of the second channel respectively according to the Airy disk central coordinates recorded.

17. The system according to claim 16, characterized in that the two-color fluorescence localized super-resolution microscope is an inverted total internal reflection fluorescence microscope;

the camera is an EMCCD camera; and/or the beam-splitting system comprises a rectangular aperture, a two-color reflector and two filters.

* * * * *